US00PP28497P3

(12) United States Plant Patent
Bautista

(10) Patent No.: US PP28,497 P3
(45) Date of Patent: Oct. 3, 2017

(54) ***ORNITHOGALUM* PLANT NAMED 'BCOR-12.001'**

(50) Latin Name: ***Ornithogalum thyrsoides* Jasq.**
Varietal Denomination: BCOR-12.001

(71) Applicant: Bay City Flower Company, Inc., Half Moon Bay, CA (US)

(72) Inventor: Rodolfo Valdoz Bautista, Half Moon Bay, CA (US)

( * ) Notice: Subject to any disclaimer, the term of this patent is extended or adjusted under 35 U.S.C. 154(b) by 140 days.

(21) Appl. No.: 14/756,794

(22) Filed: Oct. 13, 2015

(65) Prior Publication Data

US 2017/0105327 P1 Apr. 13, 2017

(51) Int. Cl.
*A01H 5/02* (2006.01)

(52) U.S. Cl.
USPC ..... Plt./462

(58) Field of Classification Search
USPC ..... Plt./462
CPC ..... A01H 5/02
See application file for complete search history.

*Primary Examiner* — Kent L Bell
(74) *Attorney, Agent, or Firm* — James R. Cypher; Charles R. Cypher

(57) ABSTRACT

A new and distinct cultivar of *Ornithogalum thyrsoides* Jasq. named 'BCOR-12.001' originated as a controlled cross between the commercial cultivar *Ornithogalum thyrsoides* Jasq. 'Beth' and a variety known as *Ornithogalum thyrsoides* Jasq. '10.1'. The cultivar 'BCOR-12.001' has R.H.S. 155 D (white group) tepals at maturity and is distinguished from other similar cultivars of which the inventor is aware by its short racemes, wide leaves and suitability for growth in pots.

3 Drawing Sheets

Botanical classification: *Ornithogalum thyrsoides* Jasq. 'BCOR-12.001'.
Variety denomination: 'BCOR-12.001'.

BACKGROUND OF THE INVENTION

This invention relates to a new and distinct cultivar of the Lilaceae family. The botanical name of the plant is *Ornithogalum thyrsoides* Jasq. 'BCOR-12.001'.

The new cultivar originated as a seedling from a controlled cross between a variety known to the inventor as *Ornithogalum thyrsoides* '10.1' and a variety known as *Ornithogalum thyrsoides* 'Beth'. '10.1' was the seed parent. '10.1' is the progeny of the commercial variety 'Bock Bay'.

The new variety was first noticed, because of its erect and short racemes.

TABLE 1

| | 'Damascus' USPP 21,448 | New Variety 'BCOR-12.001' | 'Chesapeake Snowflake' USPP 13,200 (seed parent) | 'Chesapeake Starlight' USPP 12,850 |
|---|---|---|---|---|
| Rachis/Raceme height | 40 cm | 20-25 cm | 20-30 cm | 55-60 cm |
| Rachis color | R.H.S. 146B | R.H.S. 147B | Unknown | Unknown |
| Reflexed leaves | Yes | Yes | Unknown | Unknown |
| Leaf color both sides | R.H.S. 147B | R.H.S. 147B | R.H.S. 143B | R.H.S. 143B |
| Floret diameter | 65 mm | 35 mm | 50-60 mm | 35-40 mm |
| Tepal height | 28 mm | 18 mm | 20-25 mm | 20 mm |
| Tepal Color | R.H.S. 155A | R.H.S. 155D | R.H.S. 155A-D | R.H.S. 155A-D |
| Tepal Spot Color | R.H.S. 152B | R.H.S. 152B | R.H.S. 147A | R.H.S. 152A |

The new cultivar 'BCOR-12.001' has been asexually reproduced under controlled environmental conditions at a nursery in Half Moon Bay, Calif. under the direction of the inventor with its distinguishing characteristics remaining stable.

'BCOR-12.001' is distinguished from other *Ornithogalum thyrsoides* varieties of which the inventor is aware by its short, upright racemes and its suitability for growth in pots.

Asexual reproduction was first accomplished when vegetative cuttings were taken from the initially selected plant. Examination of asexually reproduced, successive generations grown in a nursery at Half Moon Bay, Calif. show that the combination of characteristics as herein disclosed for 'BCOR-12.001' remains firmly fixed.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
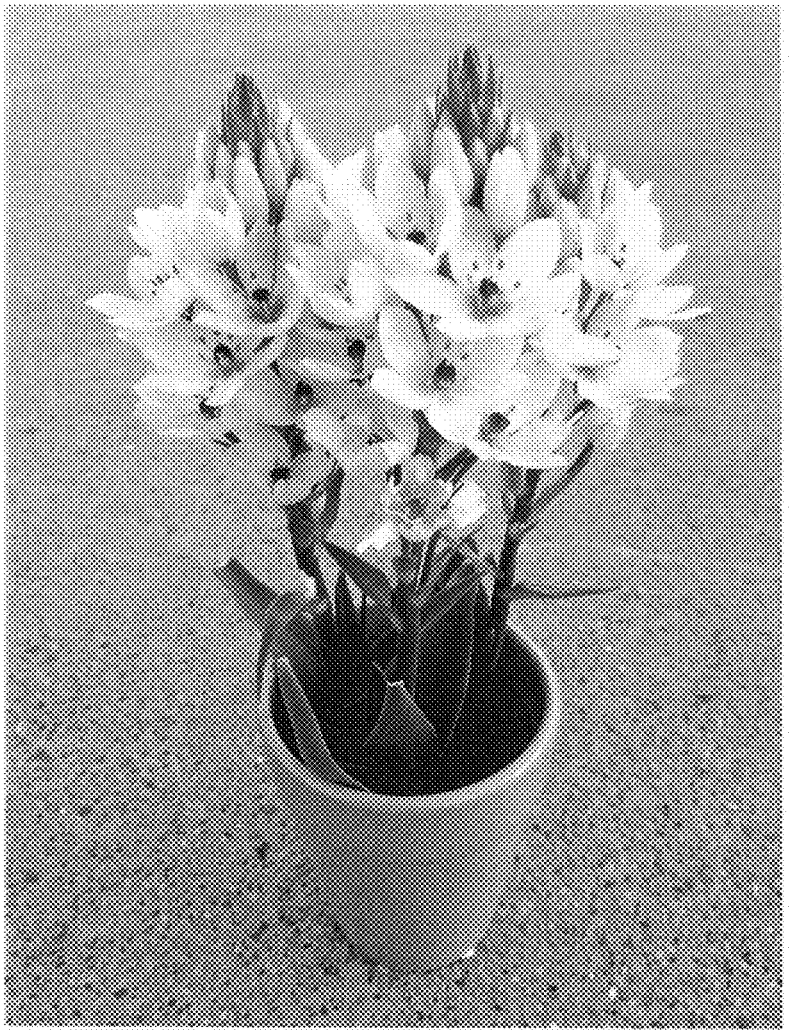
FIG. 1 is a view of the new variety showing its form, upright growth habit, dark green foliage, inflorescence, and non-pigmented tepals.
Figure 2:
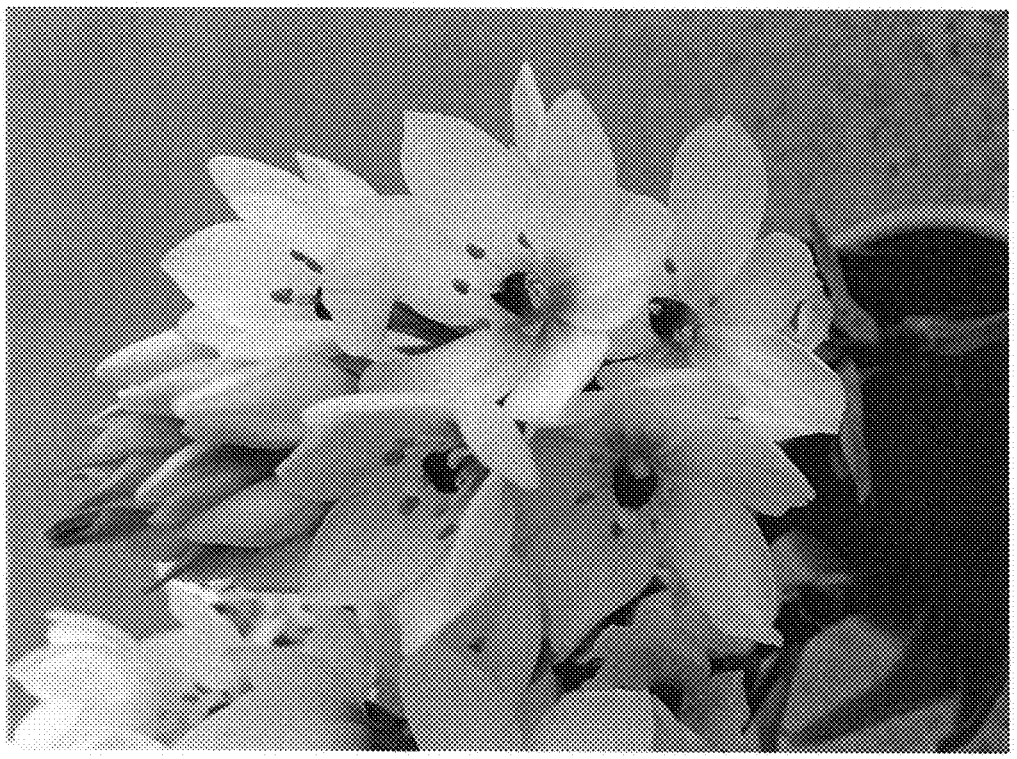
FIG. 2 is a view of the inflorescence of the new variety.
Figure 3:
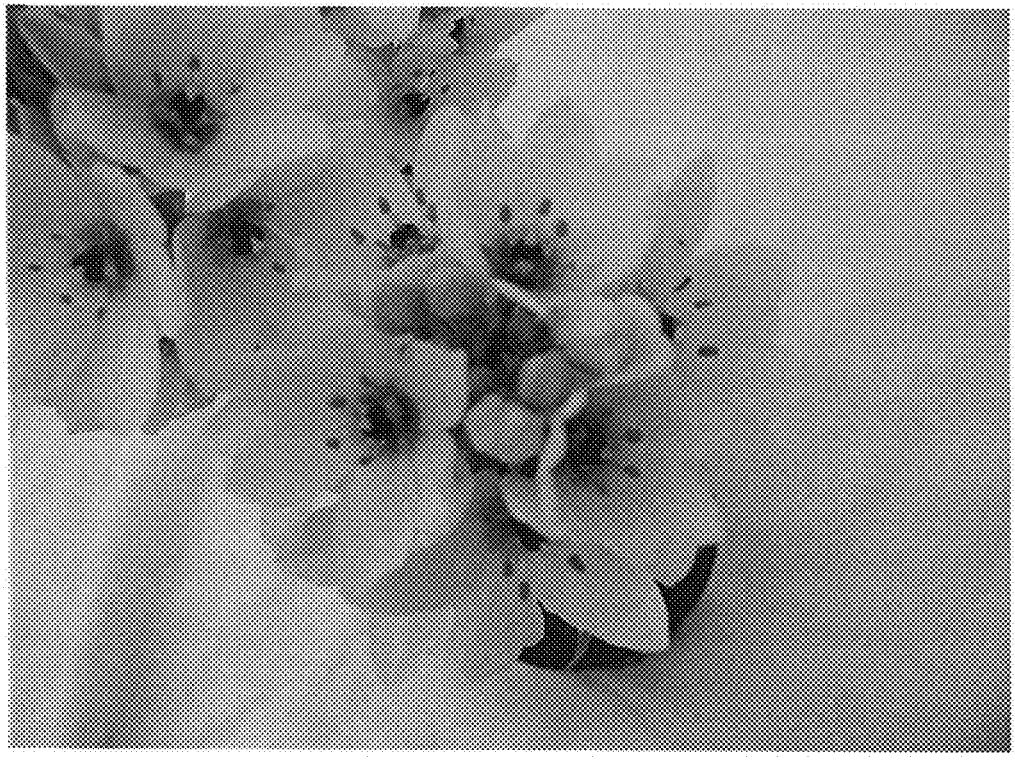
FIG. 3 is a close-up view of the inflorescence of the new variety, showing opened florets, and opening florets.
Figure 4:
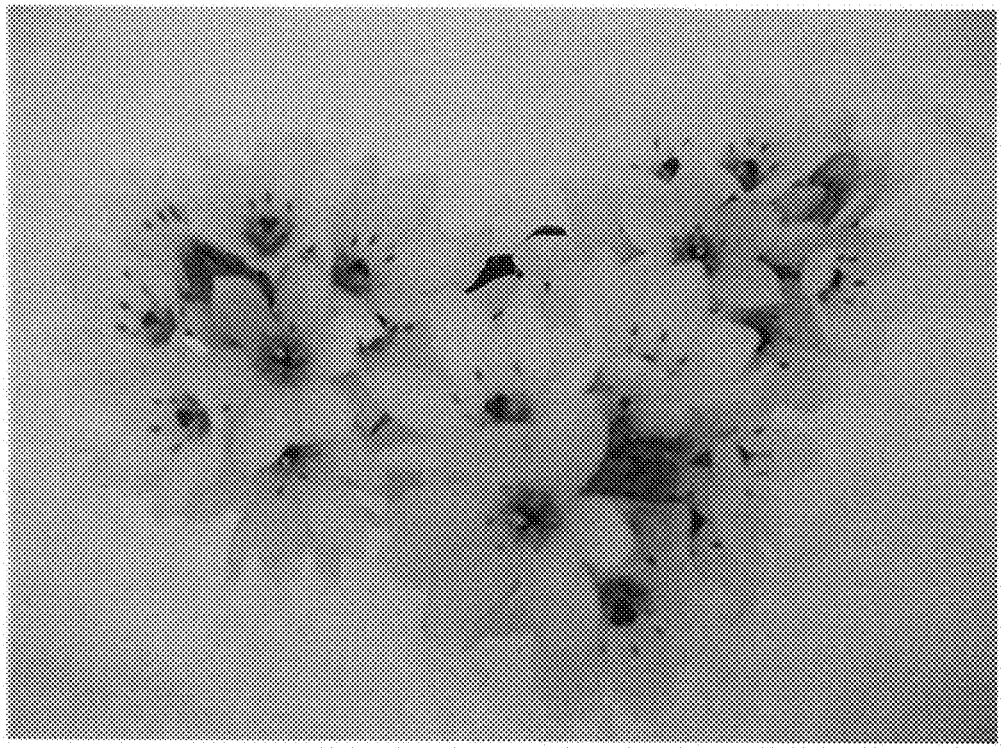
FIG. 4 is a top view of a number of inflorescences of the new variety.
Figure 5:
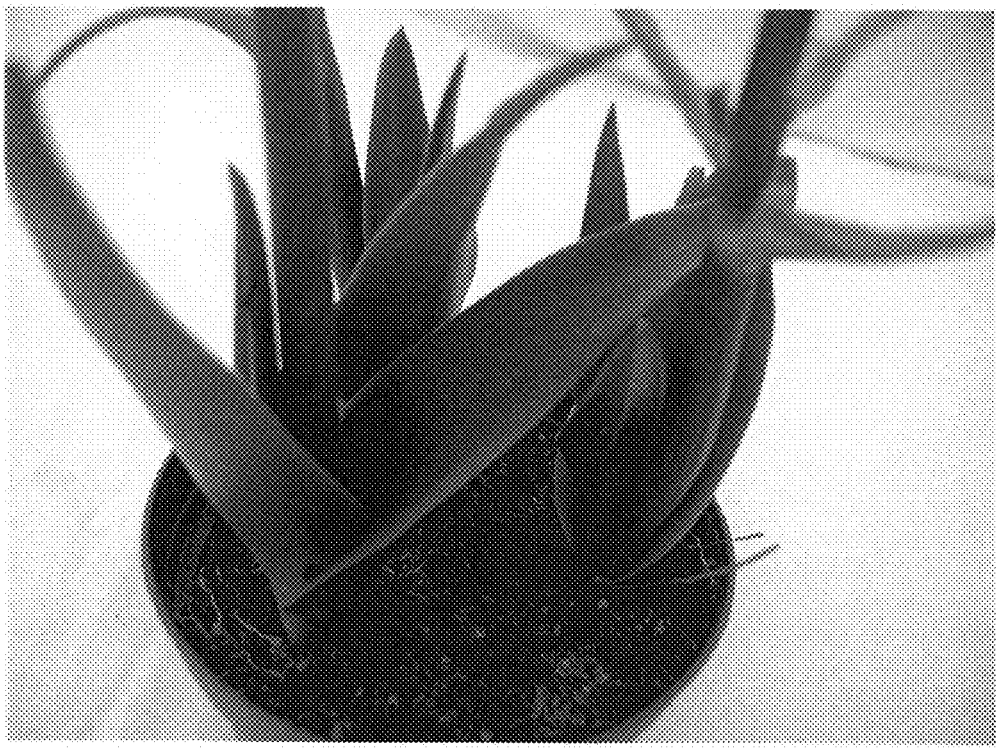
FIG. 5 is a view of the base of the new variety.

The plants shown in the figures were grown in 3" pots and were ready for commercial sale. Plants were grown from bulbs. Three bulbs were placed in each pot. Bulbs are tunicate and R.H.S. 155D (white group).

'BCOR-12.001' has not been observed under all possible environmental conditions. The phenotype may vary significantly with variations in environment such as temperature, light intensity and day length. Color determinations were made with The Royal Horticultural Society (R.H.S.) Colour Chart.

The plant:

*Origin.*—Controlled cross. Parents. — *Ornithogalum thyrsoides* Jasq. '10.1' and *Ornithogalum thyrsoides* Jasq. 'Beth' Botanic Classification. — *Ornithogalum thyrsoides* Jasq. 'BCOR-12.001'.

*Form.*—Dwarf plant with spreading basal leaves with upright inflorescences on short rachis. A typical plant with a mature inflorescence that is ready for sale is approximately 21 cm high when grown in a 3" pot with appropriate soil amendments.

*Growth.*—Upright rachis with spreading leaves. Inflorescence is large and showy. Bulbs are tunicate.

*Rachis.*—The rachis is upright and glaucescent. Its color is R.H.S. 147 B (yellow-green group). Diameter — 7 mm at base and 5 mm at top. Length to first floret and bract pair variable 5-7 cm.

*Foliage.*—Leaves alternate at base of stem, growing alongside rachis. Shape of leaf. — Fleshy, varying from channeled to flat, lanceolate. Margins are entire. Apex acute. Texture. — Glaucescent. Color. — Mature leaves are R.H.S. 147B (yellow-green group) on both sides. Large leaves are 9 cm long and 2.5 cm wide (at widest).

Inflorescence:

*Form.*—Corymbose racemes. Indeterminate. Approximately 25 to 30 individual flowers (florets) per inflorescence on pedicels that elongate as the florets opens, and on average are as long as 20 mm for mature florets. Flowers do not produce a fragrance. Young flowers are predominantly white — R.H.S. 155D (yellow-white group), 15 mm tall and have a diameter of 7 mm. The rachis for the inflorescence is strong and upright. The pedicels are predominately green — R.H.S. 144 B (yellow-green group) at maturity and glabrous. Buds are hidden by bracts.

*Size of inflorescence.*—A typical glabrous inflorescence shown in the figures of flowers at prime state for ornamentals can be as large as 7 cm in diameter, and 6 cm high.

*Shape.*—Basal florets opening first with pedicels that elongate that give the raceme a corymbose appearance as the inflorescence ages.

*Appearance.*—Showy.

Florets:

*General.*—The florets at the base of the inflorescence open first, and open more and more as the inflorescence ages. Florets are perfect and complete. Perianth is not keeled. Perianth can be highly reflexed. Each floret is associated with a bract that continually elongates and can be as long as 16 mm when flower is at its prime and is same color as pedicel — R.H.S. 144 B (yellow-green group). The bracts are lanceolate with narrowly acute apexes and are approximately 10 mm wide at their base. Perianth: There are 6 ovate tepals that are spotted at their base on both their abaxial and adaxial surfaces — R.H.S. 152 B (yellow-green group), but are predominately white on both their abaxial and adaxial surfaces — R.H.S. 155 D (white group) with the mid-vein showing on the abaxial surface. Floret diameter: 35 mm. Tepals of mature florets are typically 18 mm high, 10 mm wide at the widest and 4 mm wide at their attachment, and the spotted base is approximately 3 mm high and extends the width of the tepal at the base. Apex shape of the tepal is abruptly acuminate.

*Stamens.*—6 stamens (two sets of 3). Pollen is R.H.S. 17 A (yellow-orange group). Plant produces abundant pollen. Filament is flattened with translucent wings, alternate filaments have more prominent wings. Filament is 1 mm wide at base and 5 mm high. Filament is 2 mm at its widest point. Anther is 2 mm high and basally attached. Filament is R.H.S. 155 B (white group). Anther is R.H.S. 146 B (yellow-green group) before opening to reveal pollen.

*Stigma.*—Generally, a three-pronged stigma on one pistil per floret. The style is 1 mm long. The stigma is approximately 1 mm long. Style is 152 C (yellow-green group) and stigma is R.H.S. 155 B (white group).

*Ovary.*—The ovary is three-celled with axile placentae. The base of the ovary is R.H.S. 152 C (yellow-green group) and the top of the ovary is R.H.S. 200 B (brown group). The ovary is 5 mm high and has a diameter of 3 mm.

I claim:

1. A new and distinct *Ornithogalum* plant named 'BCOR-12.001' substantially as herein shown and described.

* * * * *